United States Patent [19]

Clark

[11] 4,212,973
[45] Jul. 15, 1980

[54] PREPARATION OF CYCLOPENTANE-1,1-DIACETIC ACID AND INTERMEDIATE

[75] Inventor: Raymond D. Clark, Kingsport, Tenn.

[73] Assignee: Eastman Kodak Company, Rochester, N.Y.

[21] Appl. No.: 62,649

[22] Filed: Aug. 1, 1979

[51] Int. Cl.$^2$ ............................................ C07D 211/58
[52] U.S. Cl. ...................................... 546/16; 562/503
[58] Field of Search .................................. 546/16, 243

[56] References Cited
PUBLICATIONS

Benica and Wilson "J. Am. Pharm. Assn." vol. 39, pp. 451–454 (1950).

Primary Examiner—Henry R. Jiles
Assistant Examiner—Robert T. Bond
Attorney, Agent, or Firm—Donald W. Spurrell; Daniel B. Reece, III

[57] ABSTRACT

Disclosed is a process comprising reacting the reaction product of cyclopentanone and methyl cyanoacetate with cyanoacetamide and/or the reaction product of cyclopentanone and cyanoacetamide with methyl cyanoacetate, in the presence of a basic catalyst, to give the intermediate $\beta,\beta$-tetramethylene-$\alpha,\alpha'$-dicyanoglutarimide, or its salt. In the process, the said reaction products may be formed together in the same reaction system, and the said intermediate preparation preferably is carried out between about 10° C. and about 50° C., in a polar, aprotic solvent, and in the presence of a basic catalyst, e.g., such as triethylamine. The intermediate may then be hydrolyzed to the cyclopentane-1,1-diacetic acid.

5 Claims, No Drawings

PREPARATION OF CYCLOPENTANE-1,1-DIACETIC ACID AND INTERMEDIATE

This invention concerns a process for the preparation of cyclopentane-1,1-diacetic acid, and particularly for the preparation of an intermediate, $\beta,\beta$-tetramethylene-$\alpha,\alpha'$-dicyanoglutarimide (or its salt).

The process comprises reacting the addition product of cyclopentanone and a cyanoacetate such as methyl cyanoacetate (methyl cyclopentylidenecyanoacetate) with cyanoacetamide and/or the addition product of cyclopentanone and cyanoacetamide (cyclopentylidenecyanoacetamide) with a cyanoacetate, e.g., methyl cyanoacetate, in the presence of a basic catalyst. In the process, the said reaction products may be formed together in the same reaction system, and the aforementioned intermediate preparation may be carried out in a wide variety of solvents such as alcohols, but preferably is carried out between about 10° C. and about 50° C., in a polar, aprotic solvent, in the presence of a basic catalyst, e.g., such as triethylamine. The isolation of compound III is accomplished by insolubilizing the salt form II by a strong acid. The acid hydrolysis to the cyclopentane-1,1-diacetic acid can be carried out with any strong acid at temperatures ranging widely, but preferably between about 100°–160°.

In a specific embodiment, the significant overall reaction sequence is thought to be as follows:

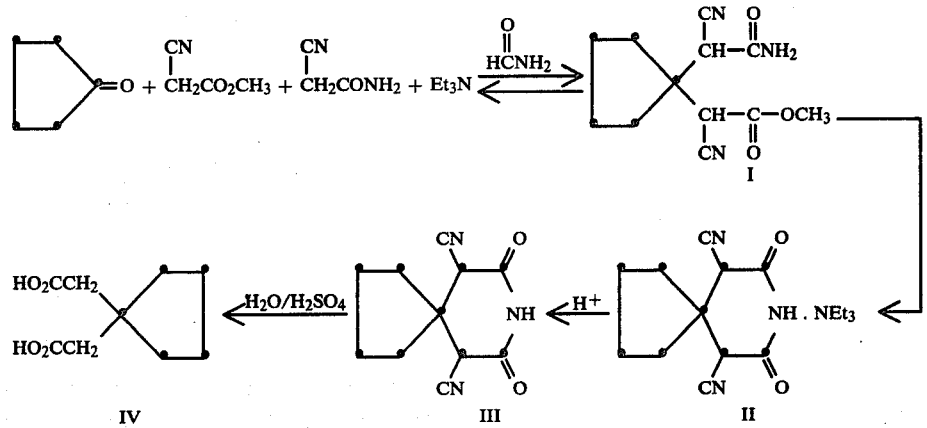

The methyl cyanoacetate reactant shown above may be any of a wide variety of esters other than methyl, e.g., practically any alkyl, straight, branched or cyclic, such as up to about 20 carbons or more including ethyl, propyl, hexyl, dodecyl, and the like, and such groups substituted with various radicals which do not react under the conditions employed such as, halogen, hydroxyl, alkoxy, alkanoyloxy, alkoxycarbonyloxy or alkenyl, all e.g., of 1–20 carbons.

The base, triethylamine, is preferred, however many other bases may be employed such as ammonia, trimethylamine, triethylenediamine, trialkylamines in general of up to about 20 carbons, preferably 1–10 carbons, which may be substituted as stated above for the alkyl groups, various alkoxides such as sodium methylate, hydroxides, trialkylphosphines, $Na_2CO_3$, metal hydrides such as sodium and calcium, and metal alkyls such as butyl lithium.

The useful polar aprotic solvents besides formamide include, e.g., dimethylformamide, dimethylsulfoxide, dimethylacetamide, N-methyl-pyrrolidone, phosphoric acid-tris-dimethylamide, and the like. Such solvents are preferred because of the increased rates of reaction.

The relative concentrations of reactants and catalyst as shown in the above reaction sequence need only be about a mole to mole ratio, other ratios being of no particular advantage, but in some cases a disadvantage in regard to competing reactions and impurities. The amount of solvent preferred is that which can maintain a solution during the formation of the salt form II.

The present process avoids the need for adding ammonia or ammonium compounds to the reaction system and the consequent need for low reaction temperatures. See, for example, the articles by H. H. Farmer, et al, and Robert E. Kent, et al. taken from "Organic Synthesis" collective Vol. 4, pg 441 et seq., and collective Vol. 3, pg 591 et seq., John Wiley & Sons, concerning the respective preparations of $\beta$-ethyl-$\beta$-methylglutaric acid and $\beta$-methylglutaric acid.

The following preparations will further illustrate the invention, all temperatures being centigrade.

1. $\beta,\beta$-Tetramethylene-$\alpha,\alpha'$-dicyanoglutarimide

A solution of 84 g. (1.0 mole) of cyclopentanone, 99 g. (1.0 mole) of methyl cyanoacetate, 84 g. (1.0 mole) of cyanoacetamide, and 300 g. of formamide is stirred and controlled at 25°–30° while to it is gradually added 101 g. (1.0 mole) of triethylamine over a period of 30 minutes. The mixture is stirred for 10 hours at 25°–30°. The temperature is then raised to 60°–65° and 600 ml. of water is gradually added. The temperature is adjusted to 60°–65° and the solution is acidified to pH 1 with 200 g. (2.0 moles) of 98% sulfuric acid with cooling as necessary to keep the temperature below 75°. The resulting slurry is cooled to 5°–10° and is filtered. The solid is washed with two 150-ml. portions of water. The amount of water in the filter cake will be about 20%. The wet cake of $\beta,\approx$-tetramethylene-$\alpha,\alpha'$-dicyanoglutarimide is used directly in the next step; yield (dry basis), 152 g. (70%).

2. Hydrolysis to cyclopentane-1,1-diacetic Acid

A mixture of 217 g. (1.0 mole) of the above $\beta,\beta$-tetramethylene-$\alpha,\alpha'$-dicyanoglutarimide, 1360 g. of 98% sulfuric acid, and 50 g. of water (the water in the wet $\beta,\beta$-tetramethylene-$\alpha,\alpha'$-dicyanoglutarimide filter cake from the previous step will account for part of the water needed in the hydrolysis) is heated at 130° for 0.5 hour. Gas is evolved. Another 50 g. of water is added and heating at 130° is continued. After another 0.5 hour, 40 g. more of water is added and heating at 130° is continued for 3 hours. A total of about 45 l. of gas is evolved. Another 450 g. of water is added and the mixture is refluxed (pot temperature 150°) for 4 hours. The mixture is cooled to 10° to crystallize, and is filtered. The solid is washed with three 100-ml. portions of cold water and is held wet for the next step; yield (dry basis), 175 g. (95%).

3. Recrystallization of Cyclopentane-1,1-diacetic Acid

A mixture of 186 g. (1.0 mole) of the above cyclopentane-1,1-diacetic acid, 500 ml. of water, 185 ml. of isopropanol, and 5 g. of activated charcoal is heated to boiling. The mixture is filtered hot (through filter aid), another 250 ml. of water is added to the filtrate, and the mixture is cooled to 10° to crystallize. Solid is filtered off and dried; yield, 167 g. (90%).

The invention has been described in detail with particular reference to preferred embodiments thereof, but it will be understood that variations and modifications can be effected within the spirit and scope of the invention.

I claim:

1. The process for preparing $\beta,\beta$-tetramethylene-$\alpha,\alpha'$-dicyanoglutarimide or its salt comprising reacting the reaction product of cyclopentanone and a cyanoacetate ester with cyanoacetamide and/or the reaction product of cyclopentanone and cyanoacetamide with a cyanoacetate ester, in the presence of a basic catalyst.

2. The process of claim 1 wherein the cyanoacetate ester is the methyl ester.

3. The process of claim 1 wherein said reaction products are formed together in the same reaction system.

4. The process of claim 1 wherein said salt is converted to the imide by acidification.

5. The process of claim 1 wherein the reaction is carried out between about 10° and about 50° C., in a polar, aprotic solvent, and in the presence of a basic catalyst selected from trialkylamines of 1–10 carbons which may be cyclic, and wherein the cyanoacetate ester is the methyl ester.

* * * * *